United States Patent [19]
Sekiguchi et al.

[11] Patent Number: 4,903,099
[45] Date of Patent: Feb. 20, 1990

[54] FIELD EFFECT TRANSISTOR FOR USE AS ION SENSOR

[75] Inventors: Tetsushi Sekiguchi, Tokorozawa; Tetsuo Hamatani, Iruma; Hideo Ozawa, Kawagoe; Masao Takahashi, Tokyo, all of Japan

[73] Assignee: Nihon Kohden Corp, Tokyo, Japan

[21] Appl. No.: 250,711

[22] Filed: Sep. 28, 1988

[51] Int. Cl.$^4$ .............................. H01L 29/66
[52] U.S. Cl. .................... 357/25; 357/23.15; 357/52; 357/54
[58] Field of Search ............. 357/54, 25, 23.15, 50, 357/47, 48, 49, 52, 52 B, 52 N

[56] References Cited

U.S. PATENT DOCUMENTS

| | | | |
|---|---|---|---|
| 4,305,802 | 12/1981 | Koshiishi | 357/25 X |
| 4,512,870 | 4/1985 | Kohara et al. | 357/25 X |
| 4,660,065 | 4/1987 | Carvajal et al. | 357/47 X |

FOREIGN PATENT DOCUMENTS 55-140142  11/1980  Japan ........................... 357/25 X

OTHER PUBLICATIONS

Wen et al., "Gate-Controlled Diodes for Ionic Concentration Measurement", *IEEE Transactions on Electron Devices*, vol. ED-26, No. 12 (Dec. 1979), pp. 1945-1951.

*Primary Examiner*—William Mintel
*Attorney, Agent, or Firm*—Hoffmann & Baron

[57] ABSTRACT

A field effect transistor for use as an ion sensor has a P-type silicon substrate on which are formed a source region and a drain region. An N-type isolation diffusion layer is formed on the outer peripheral surface of the silicon substrate and this diffusion layer is surrounded by an insulation layer. According to this arrangement, even when the potential of the electrolyte has been raised to a level which is positive with respect to the silicon substrate, an electrical isolation is established by the reverse dielectric strength exhibited by the P-N junction.

2 Claims, 2 Drawing Sheets (PRIOR ART)

FIELD EFFECT TRANSISTOR FOR USE AS ION SENSOR

The present invention relates to a field effect transistor for use as an ion sensor (referred to as ISFET, hereinafter) and, more particularly, to an ISFET suitable for use in detecting ion activity in an electrolyte.

BACKGROUND OF INVENTION

An ISFET, when immersed in an electrolyte such as blood, exhibits a change in the electrical conductivity on the semiconductor surface under the gate insulating film thereof. Notably, this change in electrical conductivity is the result of a change in the electrical potential at the boundary between the electrolyte and the insulating film. The level of ion activity in the electrolyte can be measured by making use of this change in the electrical conductivity.

The ISFET has to be electrically insulated in the electrolyte. In the Figure drawings, symbols D and S are used to denote drain and source regions, respectively. Conventionally, arrangements as shown in FIGS. 5 and 6 have been used for the purpose of electrically insulating ISFETs in electrolytes. More specifically, in the arrangement shown in FIG. 5, a silicon oxide film 2 and a silicon nitride film 3 are applied as coatings to the outer peripheral surface of the portion of a silicon substrate 1 of the ISFET immersed in the electrolyte. On the other hand, in the arrangement of FIG. 6, a ceramic substrate 4 is bonded to one side surface of the immersed portion of the silicon substrate 1 of the ISFET, while the opposing side surface is covered with a silicon oxide film 2 and a silicon nitride film 3. In addition, the entire area of the outer peripheral surface except the gate insulating film 5 is coated with an RTV rubber or an epoxy resin 6.

FIG. 7 also shows a known arrangement which employs a substrate 7 made of sapphire on which Si is made to grow. The entire surface of the silicon substrate 1 except the gate insulating film 5, is covered by a silicon oxide film 2 and a silicon nitride film 3.

These known ISFETs, however, suffer from the following disadvantages. Namely, the ISFET shown in FIG. 5 has insufficient dielectric strength because it is rather difficult to form insulating films 2, 3 of superior quality on the side surface of the element. In particular, the insulation tends to break down when the electrical potential of the electrolyte becomes positive with respect to the silicon substrate, with the result that the ISFET fails to function.

In case of the ISFET shown in FIG. 6, it is difficult to form a coating of the insulating resin 6 because the element is very small. In addition, there is a risk that the performance of the ISFET is rendered unstable due to invasion of the electrolyte in a minute gap which may be formed between the insulating resin 6 and the ceramic substrate due to insufficient bonding therebetween.

The ISFET of the type shown in FIG. 7 encounters difficulty in cutting into chips because the insulation on one side thereof is constituted by sapphire which is very hard.

In order to obviate these problems, Japanese Utility Model Publication No. 58-5245 proposes a structure of the type shown in FIG. 8. According to this proposal, an ISFET is formed having a P-type silicon substrate 1, which is surrounded at its three sides by an N-type diffusion layer 8 and a P-type diffusion layer 9, with the remainder side faced by a silicon oxide film 2 and a silicon nitride film 3. In this arrangement, an insulative layer is formed by making use of reverse dielectric strength of the PN junction formed by the P-type and N-type diffusion layers. According to this proposal, it is possible to obtain sufficient insulation between a small element and the electrolyte without requiring the outer configuration of the Si substrate to be processed. However, since the N-type diffusion layer and the P-type diffusion layer have to be formed in such a manner as to surround the silicon substrate, it is necessary to employ complex processes, such as embedding diffusion and epitaxial growth, with the result that the production process is rendered too complicated.

SUMMARY OF THE INVENTION

Accordingly, an object of the present invention is to provide an ISFET which can easily be produced and which has improved dielectric strength, while obviating various problems encountered with the known ISFETS. Examples of such problems include insufficient dielectric strength of the insulating film provided on the outer peripheral surface of the silicon substrate, and particularly the tendency for breakdown of the dielectric insulation due to rise of the potential of electrolyte to a positive level with respect to the silicon substrate. Also, such problems include the necessity in prior art ISFETS, for complicated production processes, such as forming an inverse silicon layer in order to realize a PN junction in a silicon substrate.

To this end, according to the present invention, there is provided a field effect transistor for use as an ion sensor. The field effect transistor comprises a P-type silicon substrate; a source region and a drain region formed on the P-type silicon substrate; an N-type isolation diffusion layer formed on the outer periphery of the silicon substrate; and an insulating layer formed on the outer peripheral surface of the N-type isolation diffusion layer.

According to the present invention, the isolation diffusion layer of an N-type metal is formed on the outer periphery of a P-type silicon substrate so that the insulation layer, established by the reverse dielectric strength exhibited by the P-N junction, will not break down even when the potential of the electrolyte is raised to a level which is positive with respect to the silicon substrate.

Thus, using the principles of the present invention, it is therefore possible to provide an ISFET which has a simple construction and which exhibits a high degree of electrical insulation when used in an electrolyte.

BRIEF DESCRIPTION OF THE DRAWINGS

For a fuller understanding of the objects of the present invention, reference is made to the following detailed description of the preferred embodiment which is to be taken in connection with the accompanying drawings, wherein.

DESCRIPTION OF THE PREFERRED EMBODIMENTS

Figure 8:
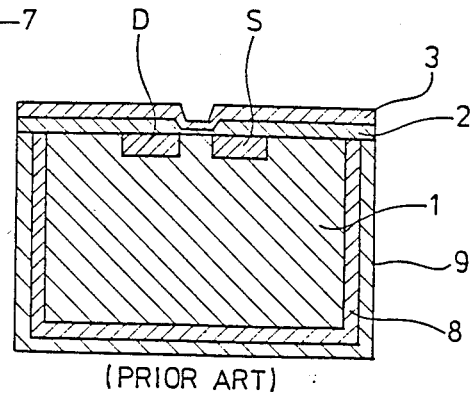

An embodiment of the ISFET in accordance with the present invention will be described with reference to FIGS. 1 and 2. In these Figures, the same reference numerals are used to denote the same parts or members as those used in the known ISFET shown in FIG. 8.

Figure 1:
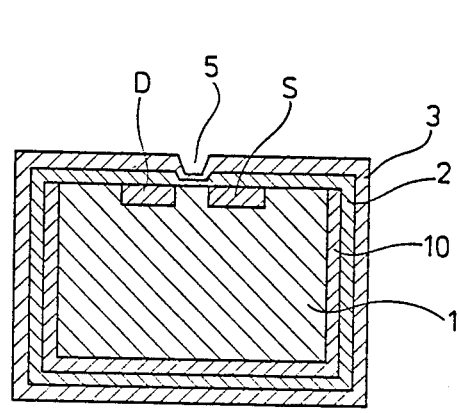
FIG. 1 is a longitudinal sectional view of an embodiment of an ISFET in accordance with the present invention.
Figure 2:
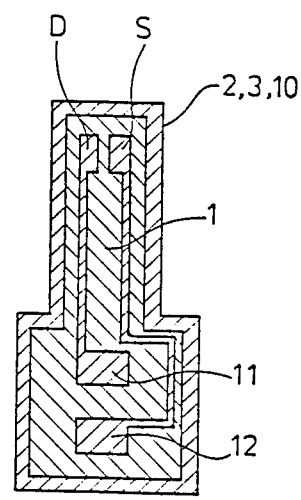
FIG. 2 is an illustration of a circuit pattern on the ISFET of FIG. 1.

Referring to FIGS. 1 and 2, the ISFET in accordance with the present invention has a drain region D and a source region S which are patterned on one side of the outer periphery of a P-type silicon substrate 1. An N-type impurity such as phosphorus is introduced to this side of the silicon substrate, by diffusion. Similarly, an N-type impurity is introduced into the other three sides of the P-type silicon substrate 1 so that an N-type diffusion layer 10 is formed on these three sides of the substrate. A silicon oxide film 2 and a silicon nitride film 3 are successively formed on four sides of the P-type silicon substrate 1 by a known thin-film forming technique such as chemical vapor deposition (CVD). Hereinafter, a description will be made of a process for producing this embodiment of the ISFET of the present invention.

Figure 3:
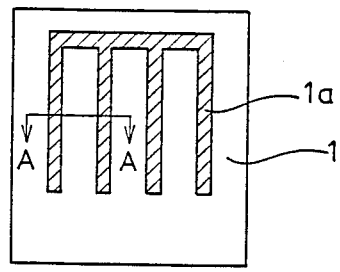
FIG. 3 is a plan view illustrating the production process in accordance with the present invention.

Referring to FIG. 3, a P-type silicon substrate is subjected to an anisotropic etching so that a comb-teeth portion 1a, as hatched, is removed from the substrate. Then, the substrate 1 is subjected to field oxidation so that an oxide film of about 1 μm thick is formed over the entire area of the substrate. A resist is then applied to the surface of the oxide film, and a known photo-lithographic method is executed so as to form the drain and source regions D and S, respectively, on one side of the substrate 1 while suitably patterning the other three sides. An example of such a pattern is shown in FIG. 2.

Figure 4:
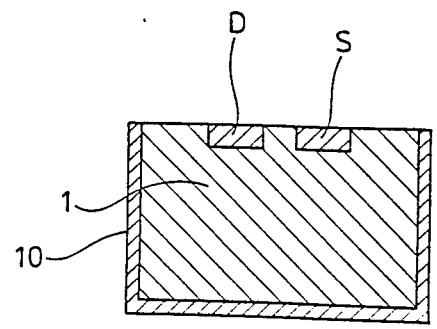
FIG. 4 is a sectional view taken along the line A—A of FIG. 3, also illustrating the production process.
Figure 5:
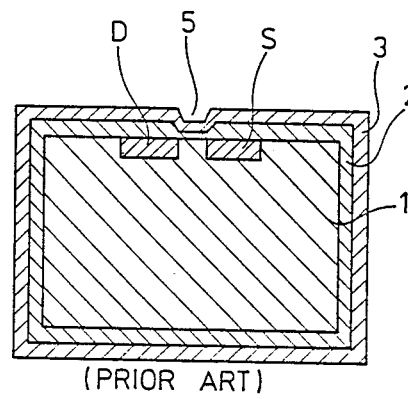
FIGS. 5 to 8 are longitudinal sectional views of known ISFETs.
Figure 6:
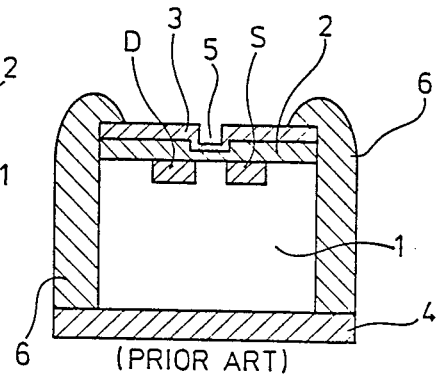
Figure 7:
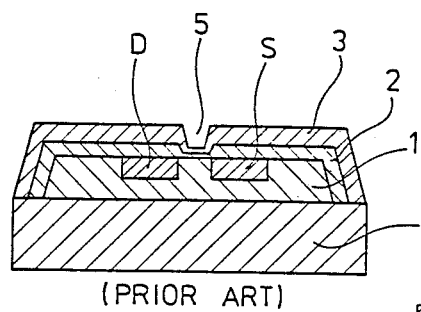

Subsequently, a developing process is executed to remove the resist, and etching of the region lacking resist is conducted using a suitable etchant such as fluoric acid, thereby removing the oxide film in the region from which the resist has been removed. Then, an N-type impurity, e.g., phosphorus, is introduced into the silicon substrate 1 so that a drain region D and a source region S with N-type impurities diffused therein, as well as N-type diffusion layer 10, are formed as shown in FIG. 4. Subsequently, a silicon oxide film 2 and a silicon nitride film 3 are sequentially formed by a known thin-film forming technique as in the case of the prior art device shown in FIG. 5, whereby the ISFET as shown in FIG. 1 is formed.

Then, pads 11 and 12 are provided through which signals are derived from the drain region D and the source region S as shown in FIG. 2.

According to this arrangement, the N-type diffusion layer 10 is provided on the outer side of the P-type silicon substrate 1 so that, when the potential of the electrolyte has become positive with respect to the silicon substrate 1, a voltage is applied to the P-N junction in a reverse-biased manner. This reverse-biased P-N junction in effect provides electrical isolation, in contrast to the conventional arrangement shown in FIG. 5. In consequence, the flow of electric current from the electrolyte to the silicon substrate 1 is prevented, and thus dielectric breakdown of the insulating films 2 and 3 is avoided.

While the particular embodiments shown and described above have proven to be useful in many applications involving the transistor manufacturing arts, further modifications herein disclosed will occur to persons skilled in the art to which the present invention pertains and also such modifications are deemed to be within the scope and spirit of the present invention defined by the appended claims.

What is claimed is:

1. A field effect transistor for use as an ion sensor, comprising:
   a P-type silicon substrate having a top, a bottom and sides;
   a source region and a drain region of N-type material formed on said top of said P-type silicon substrate;
   an N-type isolation diffusion layer formed on the outer periphery of said bottom and sides of said P-type silicon substrate; and
   an insulating layer formed on the outer peripheral surface of said N-type isolation layer.

2. A field effect transistor for use as an ion sensor according to claim 1, wherein said insulating layer is a double layer composed of a silicon nitride film and a silicon oxide film, said silicon oxide film being adjacent said P-type silicon substrate, and said silicon nitride film being adjacent said silicon oxide film.

* * * * *